(12) United States Patent
Zhu

(10) Patent No.: US 8,828,911 B2
(45) Date of Patent: Sep. 9, 2014

(54) GEL PREVENTION AGENTS

(75) Inventor: Shawn Zhu, Stormville, NY (US)

(73) Assignee: Akzo Nobel N.V., Arnhem (NL)

( * ) Notice: Subject to any disclaimer, the term of this patent is extended or adjusted under 35 U.S.C. 154(b) by 380 days.

(21) Appl. No.: 13/129,863

(22) PCT Filed: Nov. 17, 2009

(86) PCT No.: PCT/EP2009/065320
§ 371 (c)(1),
(2), (4) Date: May 18, 2011

(87) PCT Pub. No.: WO2010/057886
PCT Pub. Date: May 27, 2010

(65) Prior Publication Data
US 2011/0230354 A1    Sep. 22, 2011

Related U.S. Application Data

(60) Provisional application No. 61/116,071, filed on Nov. 19, 2008.

(30) Foreign Application Priority Data

Jan. 14, 2009 (EP) .................................. 09150538

(51) Int. Cl.
| | | |
|---|---|---|
| *A01N 25/04* | (2006.01) | |
| *C11D 1/65* | (2006.01) | |
| *A01N 25/30* | (2006.01) | |
| *C11D 1/835* | (2006.01) | |
| *C11D 1/645* | (2006.01) | |
| *A01N 25/16* | (2006.01) | |
| *C11D 1/34* | (2006.01) | |
| *C11D 1/29* | (2006.01) | |
| *C11D 1/52* | (2006.01) | |
| *C11D 1/00* | (2006.01) | |
| *A01N 33/14* | (2006.01) | |
| *C11D 1/12* | (2006.01) | |
| *C11D 1/62* | (2006.01) | |
| *C11D 1/72* | (2006.01) | |
| *C11D 1/722* | (2006.01) | |

(52) U.S. Cl.
CPC ............... *A01N 25/30* (2013.01); *C11D 1/345* (2013.01); *C11D 1/65* (2013.01); *C11D 1/29* (2013.01); *C11D 1/521* (2013.01); *C11D 1/8355* (2013.01); *C11D 1/835* (2013.01); *C11D 1/523* (2013.01); *C11D 1/008* (2013.01); *A01N 33/14* (2013.01); *C11D 1/123* (2013.01); *C11D 1/62* (2013.01); *C11D 1/526* (2013.01); *C11D 1/72* (2013.01); *C11D 1/645* (2013.01); *C11D 1/722* (2013.01)
USPC ............ 504/366; 504/118; 504/149; 504/345

(58) Field of Classification Search
CPC ........ A01N 25/30; A01N 33/12; A01N 33/14
USPC .................... 504/118, 149, 366, 345
See application file for complete search history.

(56) References Cited

U.S. PATENT DOCUMENTS

| 4,092,273 A | 5/1978 | Inamorato et al. |
| 2004/0146480 A1* | 7/2004 | Prat Queralt et al. ...... 424/70.28 |

FOREIGN PATENT DOCUMENTS

WO     WO 01/81518 A1    11/2001

OTHER PUBLICATIONS

European Search Report for EP Application No. 09150538.8; Completion date Jun. 4, 2009.
International Search Report for PCT Application No. PCT/EP2009/065320; Completion date Feb. 12, 2010.

* cited by examiner

*Primary Examiner* — Rebecca Prouty
*Assistant Examiner* — Danielle Sullivan
(74) *Attorney, Agent, or Firm* — Sugiarto Hadikusumo

(57) ABSTRACT

Gel prevention agents and methods for use with agricultural products include certain alkylamido amines and their quaternary ammonium counterparts that, when blended with products containing alkoxylated surfactants, the alkylamido amines and their quaternary counterparts reduce the gel formation tendency of such products.

20 Claims, No Drawings

GEL PREVENTION AGENTS

The present case is a 371 national phase of International patent application No. PCT/EP2009/065320 filed Nov. 17, 2009 and claims priority of European patent application No. 09150538.8 filed on Jan. 14, 2009 and U.S. patent application Ser. No. 61/116,071 filed Nov. 19, 2008.

FIELD OF THE INVENTION

The present invention generally relates to surfactants as gel prevention agents. In particular, the surfactants are certain alkylamidoamines and their quaternary ammonium counterparts. When blended with products and/or formulations containing alkoxylated surfactants, the alkylamidoamines and their quaternary ammonium counterparts can prevent or reduce the gel formation tendency of such formulations.

BACKGROUND OF THE INVENTION

Alkoxylate surfactants find applications in various industries as adjuvants, emulsifiers, dye leveling/transferring agents, and cleaning agents. However, alkoxylated surfactants typically form a gel when contacted with water. A product that is totally soluble in water could be rendered largely useless when gelling occurs. Additionally, the formation of gel makes cleaning of pipes, reaction vessels, transportation vessels and the like difficult. The formation of a gel also slows down the dissolution rate of products in water at the time of application.

To overcome the problem of gelling, diluents are often added to these products. These diluents are typically low molecular weight glycols or low molecular weight alcohols. However, such diluents are not surfactants and they don't contribute to intended properties of use. Further, adding diluents to the alkoxylated surfactants increases the cost of the formulation with no meaningful enhancement of performance.

SUMMARY OF THE INVENTION

The present invention solves the aforementioned problems. More specifically, the present inventor has unexpectedly discovered that certain alkylamidoamines and their quaternary ammonium counterparts can prevent or reduce the tendency of gel formation in products containing alkoxylated surfactants when they were contacted with water.

The present invention generally relates to gel prevention agents comprising certain alkylamidoamines and/or their quaternary ammonium counterparts. When blended with products containing alkoxylated surfactants, the alkylamidoamines and/or their quaternary ammonium surfactant counterparts prevent or reduce the gel formation tendency of such products.

DETAILED DESCRIPTION OF THE INVENTION

The invention relates to the discovery that adjuvant formulations comprising certain alkylamidoamines and their quaternary counterparts can prevent or reduce the tendency of gel formation in products containing alkoxylated surfactants when they are contacted with water. Gel prevention agents of the present invention comprise at least one alkyl amidoamine alkoxylate and/or at least one quaternary ammonium counterpart.

The alkyl amidoamine alkoxylate having utility as a gel prevention agent can be represented by the following main structure,

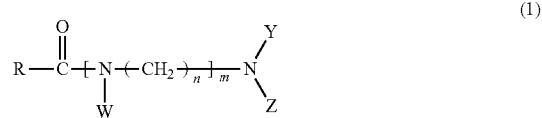

where R is a linear or branched, saturated or unsaturated alkyl group having 2-22 carbon atoms, in another embodiment 8-18 carbon atoms; m is 0-7, in another embodiment 0-3, in yet another embodiment, 1-3; n is a number 2-6, in another embodiment 2-3; W and Y are independently chosen from H, hydroxyl, an alkyl group having 1-4 carbon atoms, in another embodiment 1-2 carbon atoms and in still another embodiment 1 carbon atom, a benzyl group or $(AO)_sH$, where AO is an alkyleneoxy group having 2-4 carbon atoms, in another embodiment 2 carbon atoms, and s is on the average 1-30, in another embodiment 1-20 and in still another embodiment 5-15; Z is H, hydroxyl, an alkyl group having 1-4 carbon atoms, in another embodiment 1-2 carbon atoms and in another embodiment 1 carbon atom, a benzyl group, $(AO)_sH$, where AO is an alkyleneoxy group having 2-4 carbon atoms, in another embodiment 2 carbon atoms, and s is on the average 1-30, in another embodiment 1-20 and in yet another embodiment 5-15, or an acyl (RC=O) group. When Z is the acyl (RC=O) group, m is 1 to 7, in another embodiment 2-3.

A list of exemplary alkyl amidoamine alkoxylates includes, but is not limited to, C2 (acetic acid) amidoamine (DMAPA, dimethylamidopropylamine), C5 (NEO acid) amidoamine (DMAPA), C6 (butyric acid) amidoamine (DMAPA), C7 (caproic acid) amidoamine (DMAPA), C8 (caprylic acid) amidoamine (DMAPA), C9 (Nonanoic/Pelargonic acid) amidoamine (DMAPA), C10 (capric acid) amidoamine (DMAPA), 2EH (2-ethylhexyl acid) amidoamine (DMAPA), TOFA (toll oil fatty acid) amidoamine (DETA, diethylenetriamine) with 10☐30EO, C9 (Nonanoic/Pelargonic acid) diethanol amide, and N,N Dimethyl C10 amide.

The quaternary ammonium counterparts of the above amines having utility as a gel prevention agents have the following general structure,

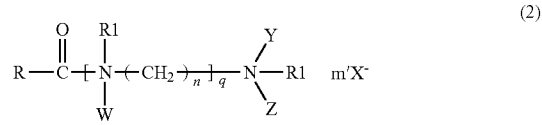

wherein R1 is a methyl or ethyl group, $X^-$ is agriculturally acceptable counter ion which can be $Cl^-$, $Br^-$, or $CH_3OSO_3^-$, $CH_3CH_2OSO_3^-$; q is an integer of from 1-6, in another embodiment 1-2, and R, W, n and Y having the same meanings as above, and m☐s 1-6, preferably 1-2.

A list of exemplary quaternary alkyl amidoamine alkoxylates includes, but is not limited to, quaternary product of TOFA (toll oil fatty acid) amidoamine (DETA) with 2 to 10EO.

The gel prevention agents of the present invention are particularly useful in preventing or reducing gel formation in products containing gel forming alkoxylated surfactants. Suitable exemplary gel forming alkoxylated surfactants may comprise alkylamine derivatives represented by the following formula:

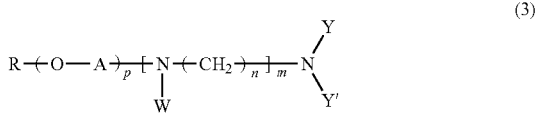

or an alkylamine quaternary surfactants of the formula:

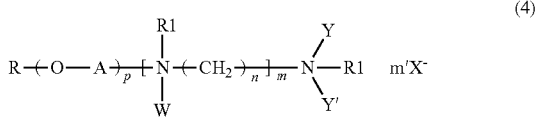

wherein R is a linear or branched, saturated or unsaturated alkyl group having 2-22 carbon atoms; A is an alkylene group having 1-4 carbon atoms; p is an integer of from 0-5; m is an integer of from 0-7; n is an integer of from 2-6; W, Y, and Y' are independently chosen from H, hydroxyl, an alkyl group having 1-4 carbon atoms, a benzyl group or $(AO)_sH$, where A is an alkylene group having 2-4 carbon atoms, and s is on the average an integer of from 1-30, m is 1-6, preferably 1-2. In other embodiments, such gel forming alkoxylated surfactants may also include mixtures of alkylamine derivatives of formula (3) and alkylamine quaternary surfactants of formula (4).

A list of exemplary gel-forming alkyl amine derivatives includes, but is not limited to, ethoxylated tallowamine, ethoxylated cocoamine, and ethoxylated alkyl etheramine. A list of exemplary gel-forming alkylamine quaternary surfactants includes, but is not limited to, quaternary of ethoxylated tallowamine, ethoxylated cocoamine, and ethoxylated alkyl etheramine.

In an exemplary embodiment of the present invention, the gel forming alkoxylated surfactant may be an alcohol alkoxylate of the formula (5)

$$R\text{—}O\text{—}(C_aH_{2a}O)_x\text{—}(C_bH_{2b}O)_y\text{—}H \quad (5)$$

wherein R is a straight or branched chain, saturated or unsaturated, substituted or unsubstituted alkyl group having from 4 to 22 carbon atoms; a and b independently are an integer of from 2 to 3; x is an integer of from 1-100 and y is an integer of from 0-100. In another exemplary embodiment, the gel forming alkoxylated surfactant may be an EO/PO block copolymer such as Pluronic 101 or Pluronic L64.

In another exemplary embodiment of the present invention, the gel forming alkoxylated surfactant may be an alkyl alkoxylated anionic surfactant exemplified by alkyl ether sulfate, alkyl ether sulfosuccinate, alkyl ethoxylated phosphate ester, and their salts. One particular useful family of the anionic surfactant is the alkyl ether sulfate exemplified by the formula (6)

$$R\text{—}O\text{—}(C_2H_4O)_j\text{—}SO_3^-M^+ \quad (6)$$

wherein R is a straight or branched chain, saturated or unsaturated, substituted or unsubstituted alkyl group having from 4 to 22 carbon atoms; j is an integer of from 1-6, in another embodiment 1-3; $M^+$ is a suitable metal ion. A list of exemplary alkyl alkoxylated sulfate includes, but is not limited to, sodium laureth sulfate with 1 to 3 EO, and ammonium laureth sulfate with 1 to 3 EO.

In an aspect of the present invention, the invention thus provides a composition having reduced gel formation tendencies comprising at least one gel forming alkoxylated surfactant and a gel prevention surfactant, the gel prevention surfactant comprising at least one alkyl amidoamine derivative of formula (1), or at least one alkyl amidoamine quaternary derivative of formula (2), or mixtures thereof. These formulations are generally used in agriculture and cleaning applications. The presence of gel prevention agent of the present invention makes a concentrated product possible without hard-to-handle gel phase.

In another aspect, the present invention provides a method for reducing the gel formation tendency of an agricultural formulation which comprises at least one gel forming alkoxylated surfactant, said method comprising adding to said formulation at least one gel prevention surfactant, said gel prevention surfactant comprising at least one alkyl amidoamine derivative of formula (1), or at least one alkyl amidoamine quaternary derivative of formula (2), or mixtures thereof.

In yet another aspect, the invention provides a pesticide formulation comprising at least one gel forming alkoxylated surfactant as an adjuvant, a gel prevention surfactant and, optionally, an herbicidal active ingredient. One particular useful area of the pesticide is as a herbicide. A typical stable herbicidal formulation according to the invention has a concentration of active in the range of 360–600 g ae/l, in another embodiment 450–580 g ae/l, and the ratio of active (wt % ae) to the adjuvant of from 2:1 and 25:1. Typically, the ratio of active (wt % ae) to the adjuvant of the invention is from 2.5:1 and 20:1, in another embodiment from 3:1 and 15:1.

In order to prevent gel formation in accordance with the invention, the gel prevention agent as described above is typically included in an amount of from 1 wt % to about 99%, preferably 5–70%, more preferably 10–50% in the surfactant blend with the gel-forming surfactants. In finished pesticide formulations, the gel prevention agent as described above is typically from about 0.05–40%, preferably 0.1–25%, more preferably 0.5–10% in the concentrated pesticide formulations.

The present invention is also suitable for the preparation of solid formulations. A typical stable solid formulation according to the invention has a concentration about 30% to 95% by weight active and about 5% to 30% by weight adjuvant.

Where an herbicidal active is included in the formulation, it is preferred that the herbicidal active be water-soluble, and more preferably that it be included in the form of an amine salt, sodium, ammonium or potassium salt. Examples of suitable herbicides are: Acetochlor, Acifluorfen, Aclonifen, Alachlor, Ametryn, Amidosulfuron, Aminopyralid, Amitrole, Anilofos, Asulam, Atrazine, Azafenidin, Azimsulfuron, Benazolin, Benfluralin, Bensulfuron-methyl, Bentazone, Bifenox, Binalafos, Bispyribac-sodium, Bromacil, Bromoxynil, Butachlor, Butroxidim, Cafenstrole, Carbetamide, Carfentrazone-ethyl, Chloridazon, Chlorimuron-ethyl, Chlorobromuron, Chlorotoluron, Chlorsulfuron, Cinidon-ethyl, Cinosulfuron, Clethodim, Clomazone, Clopyralid, Cloransulam-methyl, Clorsulfuron, Cyanazine, Cycloate, Cyclosulfamuron, Cycloxydim, Dalapon, Desmedipham, Dicamba, Dichlobenil, Dichlormid, Diclosulam, Diflufenican, Dimefuron, Dimepipeate, Dimethachlor, Dimethenamid, Diquat, Diuron, Esprocarb, Ethalfluralin, Ethametsulfuron-methyl, Ethofumesate, Ethoxysulfuron, Fentrazamide, Flazasulfuron, Florasulam, Fluchloralin, Flufenacet, Flumetsulam, Flumioxazin, Fluometuron, Flupyrsulfuron-methyl, Fluorochloridone, Fluoroxypyr, Flurtamone, Fomesafen, Foramsulfuron, Glufosinate, Hexazinone, Imazamethabenz-m, Imazamox, mazapic, Imazapyr, Imazaquin, Imazethapyr, Imazosulfuron, Iodosulfuron, Ioxynil, Isoproturon, Isoxaben, Isoxaflutole, Lactofen, Lenacil, Linuron, Mefenacet, Mesosulfuron-Methyl, Mesotrione, Metamitron, Metazachlor, Methabenzthiazuron, Metobromuron, Metolachlor, Metosulam, Metoxuron, Metribuzin, Metsulfuron-methyl, Molinate, MSMA, Napropamide, Nicosulfuron, Norflurazon, Oryzalin, Oxadiargyl, Oxadiazon, Oxasulfuron, Oxyfluorfen, Paraquat, Pendimethalin, Phenmedipham, Picloram, Pretilachlor, Profoxydim, Prometryn, Propanil, Propisochlor, Propoxycarbazone, Propyzamide, Prosulfocarb, Prosulfuron, Pyraflufen-ethyl, Pyrazosulfuron, Pyridate, Pyrithiobac, Quinclorac, Quinmerac, Rimsulfuron, Sethoxydim, Simazine, S-Metolachlor, Sulcotrione, Sulfentrazone, Sulfosulfuron, Tebuthiuron, Tepraloxydim, Terbuthylazine, Terbutryn, Thifensulfuron-methyl, Thiobencarb, Tralkoxydim, Tri-allate, Triasulfuron, Tribenuron-methyl, Triclopyr, Trifloxysulfuron, Trifluralin, Triflusulfuron-methyl, Tritosulfuron, and mixtures and combinations thereof. More preferred co-herbicides are Acetochlor, Aminopyralid, Amitrole, Atrazine, Bensulfuron-methyl, Bromoxynil, Chlorimuron-ethyl, Clethodim, Clomazone, Dicamba, Dimethenamid, Flumetsulam, Glyfosinate, Imazethapyr, Imazamox, Isoproturon, Isoxaflutole, Mesotrione, Metamitron, Metosulam, Metsulfuron-methyl, Nicosulfuron, Paraquat, Pendimethalin, Picloram, Propanil, Rimsulfuron, S-Metolachlor, Tribenuron-methyl, Triclopyr, Trifluralin, and mixtures and combinations thereof. The most preferred co-herbicides are 2,4-D, Atrazine, Aminopyralid, Amitrole, Bensulfuron-methyl, Dicamba, Flumetsulam, Glyfosinate, Imazamox, Isoproturon, Metosulam, Metsulfuronmethyl, Nicosulfuron, Pendimethalin, Rimsulfuron, Tribenuron-methyl, and mixtures and combinations thereof.

The herbicidal formulations of the present invention can, in addition to the adjuvants and gel prevention agents set forth in the above formulae, contain additional components including but not limited to, additional surfactants or other additives. It is preferred that when the formulations of the invention do contain such additional components, that such additional components are substantially non-irritating to the eye, substantially non-toxic to aquatic life, and have acceptable bio-efficacy. Such additional components include surfactants such as cationic, anionic, nonionic, and amphoteric surfactants. These surfactants are disclosed in McCutcheon's Emulsifier and Detergents, North America Edition, 2006. Non-limiting examples of preferred cationic surfactants are alkoxylated alkylamine and its quaternary derivative, alkoxylated etheramine and its quaternary derivative, alkoxylated alkyl amine oxide, alkoxylated alkyl etheramine oxide, alkyl amidopropyl amine oxide, alkyl trimethyl ammonium chloride, and alkyl dimethylamidopropylamine. Non-limiting examples of anionic surfactants are alkylsulfate, alkylethersulfate, alkylsulfonate, alkylsulfosuccinate, alkoxylated phosphate ester, alkyl alpha olefin sulfonate, alkyl n-methyl taurate, fatty acid isethionate, and alkyl ether carboxylate. Non-limiting examples of nonionic surfactants are sorbitan ester and its alkoxylated derivative, sorbitol ester and its alkoxylated derivative, fatty acid ester, castor oil alkoxylate, alcohol alkoxylate and alkyl polyglycoside. Non-limiting examples of amphoteric surfactants are alkyl betaine, alkyl amidopropyl betaine, alkylamphoacetate, alkylamphodiacetate, alkylamphocarboxylate, alkylamphopropionate, alkylamphodipropionate, alkyl amidoamine carboxylate, alkylamphohydroxypropyl sulfonate, alkyl sultaine, alkyl amidopropyl hydroxyl sultaine, alkyl dihydroxyethyl glycinate, and alkyl aminopropionate.

The herbicidal compositions of the invention can additionally comprise one or more co-herbicidal actives. Suitable co-herbicidal actives may be chosen from the above list of exemplary herbicidal actives. An herbicidal composition according to the invention can optionally comprise other additives such as ammonium sulfate, potassium sulfate, potassium chloride, sodium sulfate, urea, glycerol, glycols, polyglycols, or mixtures thereof. A contemplated composition can optionally include one or more of the following: a synergist such as tallowamine ethoxylate, quick-burn additive, humectant, co-herbicide, other pesticides, other amine compounds, e.g., dimethylamine, isopropylamine, triethylamine, diethanolamine, dye, pigment, corrosion inhibitor, thickener, dispersing agent, calcium sequestrant, defoamer, antifreeze, pour-point depressant, anti-gelling agents, pH modifiers, preservatives, hydrotropes, solvents, process aids, or mixtures thereof.

Formulations of the present invention may be generally prepared by mixing the herbicidal active as outlined above, together with other ingredients in a suitable mixing vessel with agitation, such as a blender.

This invention also relates to an herbicidal method of using a contemplated composition in an amount effective to kill or control unwanted vegetation by diluting the composition in water and applying the diluted composition to foliage of the vegetation to be killed or controlled.

The herbicidal formulation of the invention should be applied to plant foliage at an application rate sufficient to give the desired effect. Application rates are usually expressed as amount of herbicidal active ae per unit area of land treated, e.g. grams ae per hectare (g ae/ha). What constitutes a "desired effect" varies according to the standards and practice of those who investigate, develop, market, and use herbicidal products. For example, the amount of active ae applied per unit area to give, consistently and reliably, at least 85% control of a plant species as measured by growth reduction or mortality is often used to define a commercially effective rate.

Preferred compositions of the invention provide equivalent herbicidal efficacy by comparison with commercial standard formulations. "Herbicidal efficacy," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific herbicidal formulation, such as a formulation of the present invention, is within the skill of the ordinary agricultural scientist. Those of skilled in the art will likewise recognize that individual plant conditions, weather, and growing conditions, as well as the specific formulation selected, will influence the degree of biological effectiveness achieved in practicing this invention. Useful application rates can therefore depend upon all of the above conditions. Much information is known about appropriate application rates for known herbicidal formulations in general. Various application methods may be employed including broadcast spraying, directed spraying or wiping the foliage with a diluted composition of this invention. Depending on the degree of control desired, the age and species of the plants, weather conditions and other factors, typically the active application rate is an herbicidally effective amount of about 0.1 to about 10 kg ae/ha and preferably from about 0.25 to about 2.5 kg ae/ha, although greater or lesser amounts may be applied.

An example of the synthesis of the ethoxylated alkyl amidoamines (DETA) in accordance with the invention is shown below:

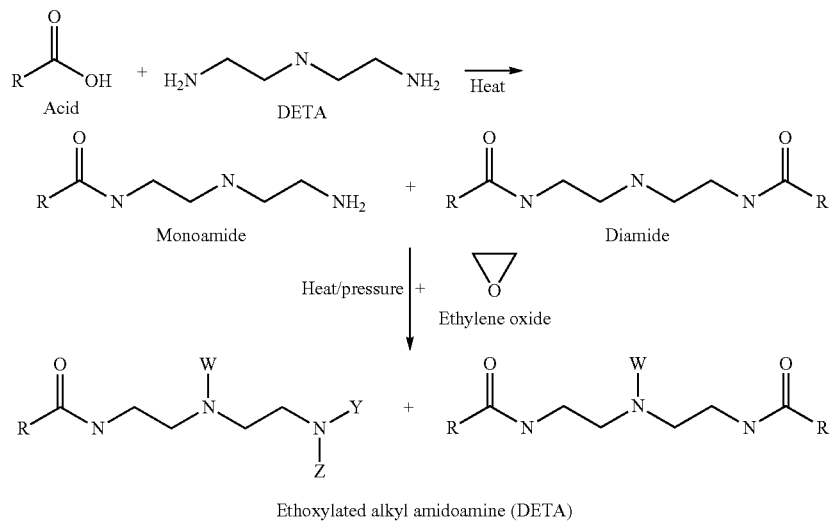

W, Y, and Z are (poly)ethylenoxy groups in this example.

An example of the synthesis of the ethoxylated alkyl amidoamines (DMAPA) in accordance with the invention is shown below:

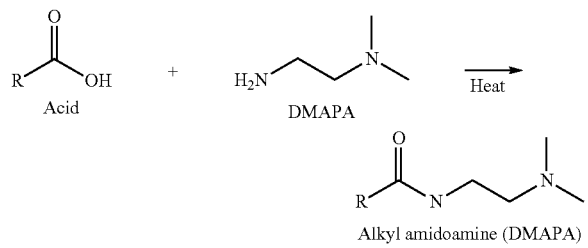

When gelling occurs, a sample is difficult to dissolve in water. The severity of gelling can be studied by observing water dissolution rate of the sample. The present invention will now be illustrated by the following non-limiting examples.

EXAMPLE 1

Water Dissolution Rate at 20° C.

In this example, the method of Water Dissolution Rate consisted of the following steps: To a 1000 ml beaker, add 1000 ml water. Stir using a magnetic bar to get a vortex reaching at the 800 ml mark. Add one drop of surfactant sample (~0.03 g) into the stirring water and at the same time start timing. Stop the watch and record the time when the sample dissolved completely.

The following dissolution rate data was obtained with surfactant samples having 70% (w/w) Ethomeen (or Ethoquad) with 30% (w/w) various gel prevention agents.

| Sample # | Sample Composition | Ethomeen T/24 (System A) | Ethoquad T/25 (System B) |
|---|---|---|---|
| 1 | Without gel prevention agent | 180 sec | 90 sec |
| 2 | Ethylene glycol | 95 | 2 |

-continued

| Sample # | Sample Composition | Ethomeen T/24 (System A) | Ethoquad T/25 (System B) |
|---|---|---|---|
| 3 | Polyethyleneglycol (400) | 0 | 3 |
| 4 | Propylene glycol | 90 | 2 |
| 5 | Diethylene glycol (DEG) butylether | 0 | 2 |
| 6 | Isopropylalcohol | 0 | 0 |
| 7 | Exxal 8 | 0 | 0 |
| 8 | NMP | 40 | 0 |
| 9 | Cocoamine-2EO | 120 | 160 |
| 10 | Tallowamine 2PO | 160 | 180 |
| 11 | Tallow Triamine-4EO | 120 | |
| 12 | C9 amidoamine (DMAPA) | 0 | 8 |
| 13 | 2EH amidoamine (DMAPA) | 2 | |
| 14 | TOFA amidoamine (DETA)-10EO | 150 | 16 |
| 15 | TOFA amidoamine (DETA)-13EO | 77 | 14 |
| 16 | TOFA amidoamine (DETA)-15EO | 11 | 11 |
| 17 | TOFA amidoamine (DETA)-18EO | 2 | 14 |
| 18 | TOFA amidoamine (DETA)-20EO | 1 | 10 |
| 19 | TOFA amidoamine (DETA)-25EO | 0 | 10 |
| 20 | TOFA amidoamine (DETA)-30EO | 0 | 14 |
| 21 | TOFA amidoamine (DETA)-2.7EO quat | 80 | 54 |
| 22 | TOFA amidoamine (DETA)-5.5EO quat | 80 | 18 |
| 23 | TOFA amidoamine (DETA)-8.6EO quat | 75 | 7.5 |
| 24 | NEO acid (C5) amidoamine DMAPA | 1 | |
| 25 | N,N Dimethyl C10 amide | 8 | |
| 26 | C9 diethanol amide | 4 | |
| 27 | C2 amidoamine DMAPA | 4 | |

TOFA admidoamine (DETA) ethoxylate was obtained by reacting toll oil fatty acid with diethylenetriamine followed by ethoxylation. C9 amidoamine (DMAPA) was obtained by reacting nonanoic acid with DMAPA.

Dissolution rate value greater than 20 seconds is considered slow because gel formed as soon as the one drop of sample contacted water. A less viscous sample may not have faster dissolution rate as it was seen in the cases of A4 (less viscous) and A20 (more viscous).

We can see that a good gel prevention agent for Ethomeen T/24 may not be a good gel prevention agent for Ethoquad T/25. We can also see that alkyladmidoamines and their quaternaries of the present invention were more effective in preventing (or reducing) the gelling of Ethomeen T/24 system than Ethoquad T/25 system.

EXAMPLE 2

☐Water Dissolution Rate at Room Temperature and at 4° C.

In this example, the method of Water Dissolution Rate consisted of the following steps: To a 100 ml beaker, add 100 ml water. Stir using a magnetic bar to get a vortex reaching at the 80 ml mark. Add one drop of surfactant sample (~0.027 g) into the stirring water and at the same time start timing. Stop the watch and record the time when the sample dissolved completely.

| Samples Description: 75% tallowamine-16EO + 25% of the following surfactant | Gel Formation @ rm temp | Dissolution Rate @ rm temp, sec | Gel formation @ 4C | Dissolution Rate @ 4C, sec |
|---|---|---|---|---|
| Tallowamine-16EO | very hard gel | 224 | | |
| DEG | hard gel | 100 | hard gel | 189 |
| TOFA amidoamine (DETA)-10.0EO | hard gel | 161 | hard gel | 228 |
| TOFA amidoamine (DETA)-13.1EO | hard gel | 114 | hard gel | 203 |
| TOFA amidoamine (DETA)-13.7EO | soft gel | 103 | hard gel | 195 |
| TOFA amidoamine (DETA)-15.0EO | hard gel | 82 | hard gel | 220 |
| TOFA amidoamine (DETA)-17.3EO | hard gel | 45 | hard gel | 168 |
| TOFA amidoamine (DETA)-20.0EO | hard gel | 42 | hard gel | 162 |
| TOFA amidoamine (DETA)-24.9EO | very soft gel | 25 | hard gel | 128 |
| TOFA amidoamine (DETA)-29.3EO | breaks up easily | 5 | soft gel | 54 |
| TOFA amidoamine (DETA)-29.5EO | breaks up easily | 6 | soft gel | 84 |

Both surfactants and the water were at the same temperatures.

It is shown in this example that TOFA amidoamine (DETA) ethoxylate reduced the gelling of tallowamine ethoxylate (16EO). It appeared that as the EO on the TOFA amidoamine (DETA) increases, the gel prevention ability increased.

EXAMPLE 3

Room Temperature Dissolution Rate (Comparison with Diethylene Glycol)

The method of Water Dissolution Rate consisted of the following steps: To a 100 ml beaker, add 100 ml water. Stir using a magnetic bar to get a vortex reaching at the 80 ml mark. Add one drop of surfactant sample (~0.027 g) into the stirring water and at the same time start timing. Stop the watch and record the time when the sample dissolved completely.

| Run # | TOFA amido amine (DETA) 15EO | Tallow amine 15EO methyl chloride | Tallow amine 15EO | Diethylene Glycol | Dissol rate, sec | Gel formation |
|---|---|---|---|---|---|---|
| 1 | 100 | | | | 4 | No |
| 2 | | 100 | | | 90 | Gel |
| 3 | | | 100 | | 100 | Gel |
| 4 | | | | 100 | 1 | No |
| 5 | 25 | 75 | | | 8 | No |
| 6 | 25 | | 75 | | 6.7 | No |
| 7 | 15 | | 85 | | 7.8 | No |
| 8 | | | 85 | 15 | 50 | Gel |
| 9 | | | 75 | 25 | 6.3 | No |

It shows in this example that TOFA amidoamine (DETA) ethoxylate-15EO has better gel prevention ability than diethylene glycol (DEG) butylether, a well known ingredient for such an application.

EXAMPLE 4

Water Dissolution Rate of Ethoxylated Alcohol and Ethylene Oxide/Propylene Oxide (EO/PO) Block Copolymers at 21° C.

In this example, the method of Water Dissolution Rate consisted of the following steps: To a 1000 ml beaker, add 1000 ml water. Stir using a magnetic bar to get a vortex reaching at the 800 ml mark. Add one drop of surfactant sample into the stirring water and at the same time start timing. Stop the watch and record the time when the sample dissolved completely.

| | 5646-94-3 | 5646-94-4 | 2204-22-28 | 2204-22-31 | 2204-22-34 | 2204-22-34 |
|---|---|---|---|---|---|---|
| C1618 + 8EO + 3PO + 12EO | 66% | 66% | | | | |
| TOFA admidoamine (DETA)-18EO | 34% | | 30% | | 30% | |
| DEG (diethylene glycol) | | 34% | | | | |
| Pluronic L101 | | | 70% | 90% | | |
| Pluronic L64 | | | | | 70% | 80% |
| C9 amidoamine (DMAPA) | | | | 10% | | 20% |
| Dissol rate, sec | 5 | 141 (gel) | 17 | 5 | 1 | 4 |

Again the data in this example showed that the alkylamidoamines were very effective in preventing the gelling of alkoxylated surfactants in water. One example showed that the alkylamidoamine was much more effective than DEG, a well known gel prevention agent.

EXAMPLE 5

Room Temperature Dissolution Rate (Comparison with Diethylene Glycol)

The method of Water Dissolution Rate consisted of the following steps: To a 100 ml beaker, add 100 ml water. Stir using a magnetic bar to get a vortex reaching at the 80 ml mark. Add one drop of surfactant sample into the stirring water and at the same time start timing. Stop the watch and record the time when the sample dissolved completely.

|  | 2204-33-1 | 2204-33-2 | 2204-33-8 | 2204-74-4 |
|---|---|---|---|---|
| Witcolate LES-60C (60% sodium laureth-3 sulfate in ethanol) | 100% | 85% | 85% | 85% |
| Propylene glycol |  | 15% |  |  |
| C9 amidoamine (DMAPA) |  |  | 15% |  |
| C6 amidoamine (DMAPA) |  |  |  | 15% |
| Dissol rate, sec | 150 | 68 | 43 | 46 |

Again the data in this example showed that the alkylamidoamines were very effective in preventing the gelling of alkoxylated anionic surfactants in water. The alkylamidoamines were more effective than propylene glycol, a well known gel prevention agent.

The invention claimed is:

1. A formulation having reduced gel formation tendencies comprising:
   at least one gel forming alkoxylated surfactant;
   an agrochemically active ingredient; and
   a gel prevention surfactant,
said gel prevention surfactant comprising at least one alkyl amidoamine derivative of formula (1), or at least one alkyl amidoamine quaternary derivative of formula (2), or mixtures thereof, wherein the alkyl amidoamine derivative of formula (1) is represented by the formula:

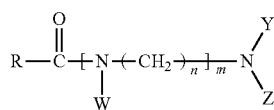

where R is a linear or branched, saturated or unsaturated alkyl group having 2-22 carbon atoms; m is an integer of from 0-7; n is a integer of from 2-6; W and Y are independently chosen from H, hydroxyl, an alkyl group having 1-4 carbon atoms, a benzyl group or $(AO)_sH$, where AO is an alkyleneoxy group having 2-4 carbon atoms, where s is on the average an integer of from 1-30; Z is independently chosen from H, hydroxyl, an alkyl group having 1-4 carbon atoms, a benzyl group, $(AO)_sH$, where AO is an alkyleneoxy group having 2-4 carbon atoms, where s is on the average an integer of from 1-30, or an acyl group; and said at least one alkyl amidoamine quaternary derivative of formula (2) is represented by the formula:

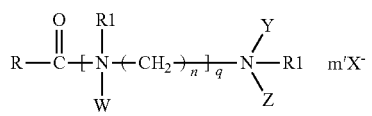

where R1 is chosen from methyl or ethyl, X— is an agriculturally acceptable counter ion, q is an integer of from 1-6, m' is an integer of 1-6, and R, W, n, Y, and Z are the same as above.

2. The formulation of claim 1 wherein, in formula (1), (2), or both, R is a linear or branched, saturated or unsaturated alkyl group having 8-18 carbon atoms; m is an integer of 0-3; n is an integer of 2-3; W and Y are independently chosen from H, hydroxyl, an alkyl group having 1-2 carbon atoms, a benzyl group or $(AO)_sH$, where AO is an alkyleneoxy group having 2 carbon atoms, and s is on the average an integer of from 1-20; Z is independently chosen from H, hydroxyl, an alkyl group having 1-2 carbon atoms, a benzyl group, $(AO)_sH$, where AO is an alkyleneoxy group having 2 carbon atoms, and s is on the average an integer of 1-20, or an acyl group.

3. The formulation of claim 1 wherein when Z is an acyl group, m is an integer of 1 to 7.

4. The formulation of any one of claim 1 wherein the weight ratio of the gel prevention surfactant and the gel forming surfactant is between 1:99 and 99:1.

5. The formulation of claim 1 wherein said at least one gel forming alkoxylated surfactant comprises an alkylamine derivative of formula (3):

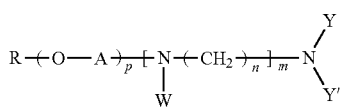

or an alkylamine quaternary surfactant of formula (4)

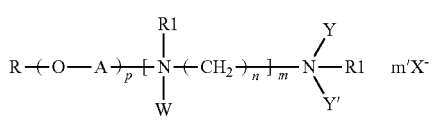

wherein R is a linear or branched, saturated or unsaturated alkyl group having 2-22 carbon atoms; A is an alkylene group having 1-4 carbon atoms; p is an integer of 0-5; m is an integer of 0-7; n is an integer of 2-6; W, Y and Y' are independently chosen from H, hydroxyl, an alkyl group having 1-4 carbon atoms, a benzyl group or $(AO)_sH$, where A is an alkylene group having 2-4 carbon atoms, and s is on the average an integer of from 1-30, and m' and X have the meaning as presented in claim 1.

6. The formulation of claim 1 wherein said gel forming alkoxylated surfactant is an alcohol alkoxylate of formula (5)

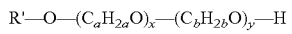

wherein R' is a straight or branched chain, saturated or unsaturated, substituted or unsubstituted alkyl group having from 4 to 22 carbon atoms; a and b independently are an integer of 2 to 3; x is an integer of 1-100 and y is an integer of 0-100.

7. The formulation of claim 1 wherein said gel forming alkoxylated surfactant is an EO/PO block copolymer.

8. The formulation of claim 1 wherein the agrochemically active ingredient, is an herbicidal active ingredient.

9. The agricultural formulation of claim 1 wherein the active ingredient is present in an amount of from 360 to 600 ae/l and the ratio of active ingredient to gel forming surfactant is from 2:1 to 25:1.

10. The agricultural formulation of claim 1 wherein said active ingredient is present in an amount of from 30 wt % to 95 wt % of the formulation and the gel forming surfactant is present in an amount of from 5 wt % to 30 wt % of the formulation and wherein said agricultural formulation is a solid.

11. The agricultural formulation of claim 1 wherein said agricultural formulation is an aqueous concentrate having an herbicidal active equivalent in a range of from 30% to 45% by weight of the composition and a gel forming surfactant in a range of from 1.2% to 22.5% by weight of the composition.

12. The agricultural formulation of claim 1 wherein the gel forming alkoxylated surfactant is an alkyl alkoxylated anionic surfactant.

13. The agricultural formulation of claim 12 wherein the alkyl alkoxylated anionic surfactant is an alkyl ether sulfate of the formula (6)

$$R'-O-(C_2H_4O)_j-SO_3^-M^+ \quad (6)$$

wherein R' is a straight or branched chain, saturated or unsaturated, substituted or unsubstituted alkyl group having 4 to 22 carbon atoms; j is an integer of 1-6, and $M^+$ is a suitable metal ion.

14. The agricultural formulation of claim 12 wherein the gel forming alkoxylated surfactant is chosen from alkyl ether sulfate, alkyl ether sulfosuccinate, alkyl ethoxylated phosphate ester, salts thereof, and mixtures thereof.

15. The agricultural formulation of claim 13 wherein the gel forming alkyl alkoxylated sulfate is chosen from sodium laureth sulfate with 1 to 3 EO, ammonium laureth sulfate with 1 to 3 EO, and mixtures thereof.

16. A method for reducing the gel formation tendency of a formulation which comprises at least one gel forming alkoxylated surfactant and an agrochemically active ingredient, said method comprising the incorporation, in said formulation, of at least one gel prevention surfactant, said gel prevention surfactant comprising at least one alkyl amidoamine derivative of formula (1), or at least one alkyl amidoamine quaternary derivative of formula (2), or mixtures thereof, wherein the alkyl amidoamine derivative of formula (1) is represented by the formula:

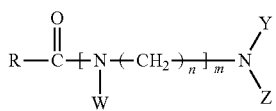

(1)

where R is a linear or branched, saturated or unsaturated alkyl group having 2-22 carbon atoms; m is an integer of from 0-7; n is a integer of from 2-6; W and Y are independently chosen from H, hydroxyl, an alkyl group having 1-4 carbon atoms, a benzyl group or $(AO)_sH$, where AO is an alkyleneoxy group having 2-4 carbon atoms, where s is on the average an integer of from 1-30; Z is independently chosen from H, hydroxyl, an alkyl group having 1-4 carbon atoms, a benzyl group, $(AO)_sH$, where AO is an alkyleneoxy group having 2-4 carbon atoms, where s is on the average an integer of from 1-30, or an acyl group; and said at least one alkyl amidoamine quaternary derivative of formula (2) is represented by the formula:

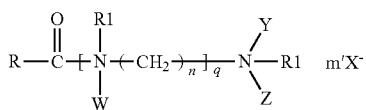

(2)

where R1 is chosen from methyl or ethyl, X— is an agriculturally acceptable counter ion, q is an integer of from 1-6, m' is an integer of 1-6, and R, W, n, Y, and Z are the same as above.

17. The method of claim 16 wherein, in formula (1), (2), or both, R is a linear or branched, saturated or unsaturated alkyl group having 8-18 carbon atoms; m is an integer of 0-3; n is an integer of 2-3; W and Y are independently chosen from H, hydroxyl, an alkyl group having 1-2 carbon atoms, a benzyl group or $(AO)_sH$, where AO is an alkyleneoxy group having 2 carbon atoms, and s is on the average an integer of from 1-20; Z is independently chosen from H, hydroxyl, an alkyl group having 1-2 carbon atoms, a benzyl group, $(AO)_sH$, where AO is an alkyleneoxy group having 2 carbon atoms, and s is on the average an integer of 1-20, or an acyl group.

18. The method of claim 16 wherein when Z is an acyl group, m is an integer of 1 to 7.

19. The method of claim 16 wherein said at least one gel forming alkoxylated surfactant comprises an alkylamine derivative of formula (3):

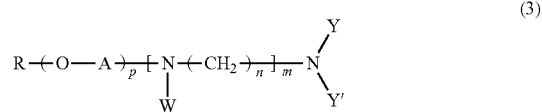

(3)

or an alkylamine quaternary surfactant of formula (4)

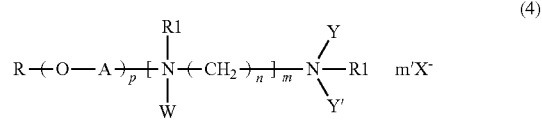

(4)

wherein R is a linear or branched, saturated or unsaturated alkyl group having 2-22 carbon atoms; A is an alkylene group having 1-4 carbon atoms; p is an integer of 0-5; m is an integer of 0-7; n is an integer of 2-6; W, Y and Y' are independently chosen from H, hydroxyl, an alkyl group having 1-4 carbon atoms, a benzyl group or $(AO)_sH$, where A is an alkylene group having 2-4 carbon atoms, and s is on the average an integer of from 1-30, and m' is an integer of from 1-6 and X— is an agriculturally acceptable counter ion.

20. The formulation of claim 1 wherein said gel forming alkoxylated surfactant is an alcohol alkoxylate of formula (5)

$$R'-O-(C_aH_{2a}O)_x-(C_bH_{2b}O)_y-H \quad (5)$$

wherein R' is a straight or branched chain, saturated or unsaturated, substituted or unsubstituted alkyl group having from 4 to 22 carbon atoms; a and b independently are an integer of 2 to 3; x is an integer of 1-100 and y is an integer of 0-100.

* * * * *